United States Patent
Wang et al.

(10) Patent No.: US 8,642,029 B2
(45) Date of Patent: Feb. 4, 2014

(54) **TRANSIENTLY BUFFERED *LACTOBACILLUS* PREPARATIONS AND USE THEREOF**

(75) Inventors: Jun Wang, Sunnyvale, CA (US); Yang Liu, Mountain View, CA (US); Qiang Xu, Cupertino, CA (US)

(73) Assignee: Osel, Inc., Santa Clara, CA (US)

( * ) Notice: Subject to any disclaimer, the term of this patent is extended or adjusted under 35 U.S.C. 154(b) by 463 days.

(21) Appl. No.: 12/935,516

(22) PCT Filed: Mar. 30, 2009

(86) PCT No.: PCT/US2009/038822
§ 371 (c)(1),
(2), (4) Date: Feb. 18, 2011

(87) PCT Pub. No.: WO2009/123982
PCT Pub. Date: Oct. 8, 2009

(65) Prior Publication Data
US 2011/0135615 A1    Jun. 9, 2011

Related U.S. Application Data

(60) Provisional application No. 61/041,097, filed on Mar. 31, 2008.

(51) Int. Cl.
*A01N 63/00*    (2006.01)
(52) U.S. Cl.
USPC ..................... 424/93.45; 435/252.9
(58) Field of Classification Search
None
See application file for complete search history.

(56) References Cited

U.S. PATENT DOCUMENTS

| | | | |
|---|---|---|---|
| 5,501,857 A | 3/1996 | Zimmer | |
| 5,592,949 A | 1/1997 | Moench et al. | |
| 5,614,209 A | 3/1997 | Ford | |
| 5,635,202 A | 6/1997 | Ford | |
| 5,733,774 A | 3/1998 | Jin et al. | |
| 5,958,461 A | 9/1999 | Larsen | |
| 6,610,531 B1 | 8/2003 | Mateczun et al. | |
| 7,122,370 B2 | 10/2006 | Porbucan | |
| 7,229,818 B2 | 6/2007 | Porubcan | |
| 2002/0090365 A1 | 7/2002 | Chrisope | |
| 2004/0071679 A1* | 4/2004 | De Simone | 424/93.45 |
| 2004/0253217 A1 | 12/2004 | Samuelsson et al. | |
| 2006/0182786 A1 | 8/2006 | Rademacher | |

FOREIGN PATENT DOCUMENTS

| | | |
|---|---|---|
| WO | WO 96/23868 A1 | 8/1996 |
| WO | WO 2005/034861 A2 | 4/2005 |

OTHER PUBLICATIONS

"Dissociation Constants of Organic Acids and Bases," in CRC Handbook of Chemistry and Physics, 94th Edition (Internet Version 2014), W.M. Haynes, ed., CRC Press/Taylor and Francis, Boca Raton, FL. Accessed on Jul. 3, 2013. pp. 5-94.*
Moore, D.D. Commonly Used Reagents and Equipment. Current Protocols in Molecular Biology. 2001. 35: A.2.1-A.2.8.*
The International Search Report from PCT/US2009/038822US, dated Dec. 23, 2009 (1 page).

* cited by examiner

*Primary Examiner* — Allison Ford
*Assistant Examiner* — Susan E Fernandez
(74) *Attorney, Agent, or Firm* — Kilpatrick Townsend & Stockton LLP

(57) ABSTRACT

The present invention relates to methods and compositions for *Lactobacillus* Replacement Therapy (LRT). Methods for improved stability and recovery of dried bacterial preparations are also provided.

10 Claims, 4 Drawing Sheets

Bacterial plating without dilution

In simulated vaginal fluid, pH 4.2
~280 mOsm

Bacterial plating with 1:1000 dilution

In MRS broth, pH 6.2
~470 mOsm

SVF, pH 4.2

SVF + 10 mM Arg,
pH 4.74

SVF + 10 mM Arg-HCl,
pH 4.15

SVF + 10 mM
Asp, pH 4.29

SVF + 10 mM
$NaHCO_3$, pH 4.74

SVF + 10 mM
$Na_2HPO_4$,

TRANSIENTLY BUFFERED *LACTOBACILLUS* PREPARATIONS AND USE THEREOF

CROSS-REFERENCES TO RELATED APPLICATIONS

This application is the U.S. National Stage entry under §371 of International Application No. PCT/US2009/038822, filed Mar. 30, 2009, which claims benefit of U.S. Provisional Application No. 61/041,097, filed Mar. 31, 2008, each of which is herein incorporated by reference in its entirety.

FIELD OF THE INVENTION

The invention is directed toward compositions and methods for carrying out *Lactobacillus* Replacement Therapy (LRT). The invention also provides compositions and methods for the improved stability and recovery of dried bacterial preparations.

BACKGROUND OF THE INVENTION

The mucosal membranes of all humans are naturally colonized by bacterial microflora. Recent studies have indicated that these microflora interact closely with cells and tissues of the body to regulate natural biological processes such as non-specific host defense. See, e.g., Redondo-Lopez, et al. (1990) *Rev. Infect. Dis.* 12:856-872. Epidemiological evidence suggests that the normal vaginal microbial ecosystem may play a critical role in reducing the risk of sexually transmitted infections, including human immunodeficiency virus-1 (HIV-1). Indeed, depletion of vaginal *Lactobacillus* is associated with development of clinical syndromes, such as bacterial vaginosis (BV), establishment of opportunistic infections, and an increased risk of acquiring HIV-1 and Herpes simplex virus type 2 (HSV-2) in women. See, e.g., Sha et al. (2005) *J. Infect. Dis.* 191:25-32; Taha et al. (1998) *AIDS* 12:1699-1706.

There has been considerable interest in the development of non-antibiotic, ecologically appropriate approaches, such as *Lactobacillus* Replacement Therapy (LRT) to replenish healthy vaginal flora and to prevent urogenital infections. The vagina, together with its microflora, constitutes a dynamic ecosystem with important host defense capabilities that promote reproductive health. In healthy women of child-bearing age, the vaginal flora is dominated by $10^{-7}$-$10^{-9}$ colony forming units (CFU) of *Lactobacillus* per gram of fluid. The species of *Lactobacillus* most commonly isolated from the reproductive tracts of healthy women worldwide includes *L. crispatus, L. jensenii, L. gasseri,* and *L. iners*. See, e.g., Antonio et al., (1999) *J. Infect. Dis.* 180:1950-1956; Vasquez et al., (2002) *J. Clin. Microbiol.* 40:2746-2749. These species are phylogenetically different from food and/or environmental *Lactobacillus* species. These facultative anaerobes metabolize glucose to lactic acid, contributing to the maintenance of a low vaginal pH (4.0-4.5) that accounts for a major part of the non-specific defense of the vagina. An acidic pH has a significant antiviral effect against HIV, HSV-2, and other urogenital pathogens. Therefore, beneficial lactobacilli associated with the vaginal mucosa can be considered to provide a protective "biofilm". See e.g., Falagas et al., (2006) *Drugs,* 66:1253-1261.

The success of LRT depends in part on selection of an ecologically appropriate *Lactobacillus* strain, cell preservation, cell recovery of the dried and formulated *Lactobacillus* following rehydration, as well as the extent and duration of vaginal colonization.

Various methods for administering beneficial bacteria and other substances to the vaginal mucosa are known. For example, dried *Lactobacillus* have been administered as vaginal tablets, capsules, and as vaginal suppositories. A major drawback of each of these preparations is a low percentage of physiologically viable cells reflected by a low recovery in simulated vaginal fluid, significantly affecting the actual bacterial dosage. The present invention addresses these and other needs.

BRIEF SUMMARY OF THE INVENTION

In one aspect, the present invention provides for a method to colonize vaginal mucosa with a desired microbial species by contacting a vaginal wall with a dried formulation of live microbial cells. The dried formulation comprises at least one buffering agent having a $pk_a$ of at least 4.3 and wherein 140 mg of the dried microbial formulation dissolved in 3 ml of water maintains a pH of at least 4.3 with the addition of 60 µl of 0.1N HCl.

Another aspect of the present invention, provides for an improved method of preserving a viable microbial species suitable for use in *Lactobacillus* Replacement Therapy. The method comprises suspending the desired live microbial cells in a preservation matrix comprising at least one buffering agent having a pH of at least 4.3, and drying the formulation. One hundred forty mg of the dried formulation, dissolved in 3 ml of water, can maintain a pH of at least 4.3 with the addition of 60 µl of 0.1N HCl.

Another aspect of the present invention provides for a method of improving the cell recovery upon rehydration of a dried microbial preparation in an acidic environment. The method comprises adding at least one buffering agent having a $pk_a$ of at least 4.3 to a dried microbial preparation. The resulting formulation is such that 140 mg of the dried preparation dissolved in 3 ml of water, can maintain a pH of at least 4.3 with the addition of 60 µl of 0.1N HCl.

Another aspect of the present invention is a dried microbial composition comprising at least one buffering agent having a $pk_a$, of at least 4.3. The dried composition is such that 140 mg of the dried preparation dissolved in 3 ml of water, can maintain a pH of at least 4.3 with the addition of 60 µl of 0.1N HCl.

The following embodiments can be combined with any of the above aspects of the invention. For example, in some embodiments, the microbial species is of the genus *Lactobacillus*. In some embodiments, the *Lactobacillus* species is selected from the group consisting of *L. crispatus, L. jensenii, L. gasseri, L. johnsonii, L. fermentum, L. vaginalis, L. gallinaruin, L. coleohoininis, L. acidophilus,* and *L. iners*.

In some embodiments, the buffering agent is selected from the group consisting of $Na_2HPO_4$, $NaHCO_3$, phosphate salts, and arginine. In some embodiments, the buffering agent is present in a concentration range from about 10 mM to about 200 mM. In some embodiments, the buffering agent is present in a concentration range from about 25 mM to about 200 mM.

In some embodiments, 140 mg of the dried formulation dissolved in 3 ml of water will maintain a pH above 4.4 with the addition of 60 µl of 0.1N HCl. In some embodiments, 140 mg of the dried formulation dissolved in 3 ml of water will maintain a pH above 4.5 with the addition of 60 µl of 0.1N HCl. In some embodiments, 140 mg of the dried formulation dissolved in 3 ml of water will maintain a pH above 4.6 with the addition of 60 µl of 0.1N HCl. In some embodiments, 140 mg of the dried formulation dissolved in 3 ml of water will maintain a pH above 4.7 with the addition of 60 µl of 0.1N HCl. In some embodiments, 140 mg of the dried formulation dissolved in 3 ml of water will maintain a pH above 6.0 with the addition of 60 µl of 0.1N HCl. In some embodiments, 140 mg of the dried formulation dissolved in 3 ml of water will maintain a pH above 7.0 with the addition of 60 µl of 0.1N HCl. In some embodiments, 140 mg of the dried formulation dissolved in 3 ml of water will maintain a pH above 8.0 with the addition of 60 µl of 0.1N HCl.

DETAILED DESCRIPTION OF THE INVENTION

I. Definitions

Figure 1:
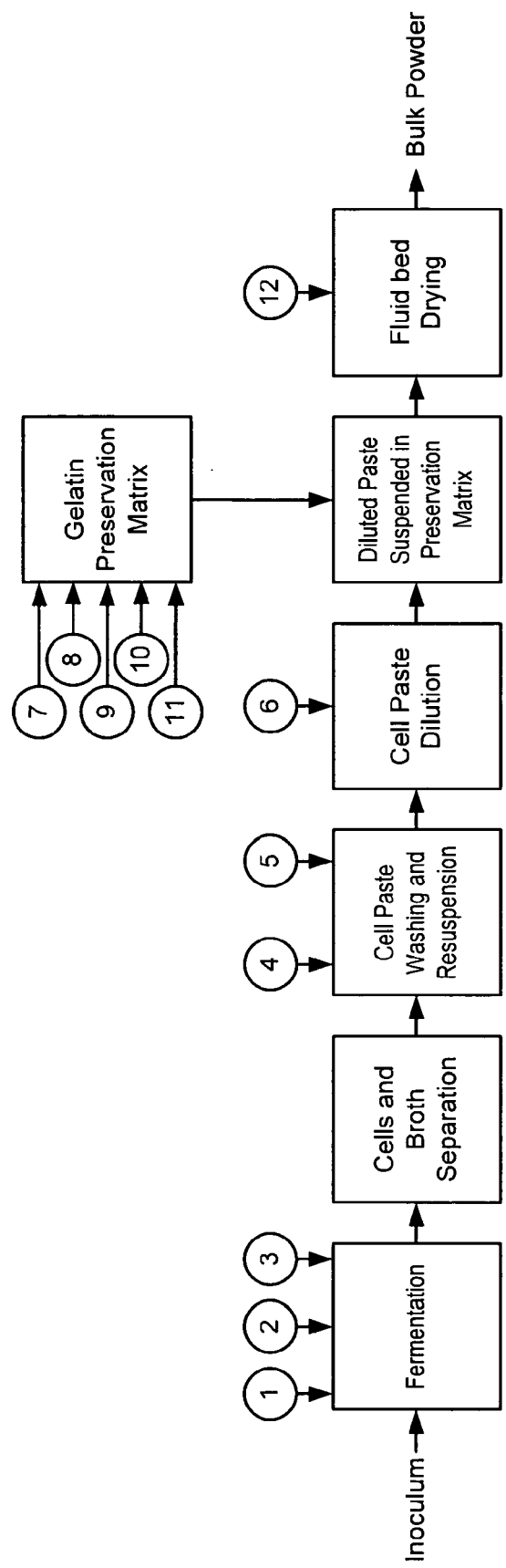
FIG. 1 provides a general process flow diagram for pilot-scale production of *L. crispatus* CTV-05 and *L. jensenii* 1153. Chemicals fed into the production include: (1) fresh medium, (2) base control solution, (3) glucose control solution, (4) and (5) phosphate buffer, (6) PBS (optional), (7) xylitol solution, (8) trehalose solution, (9) non fat dried milk solution, (10) gelatin solution, (11) sodium ascorbate, and (12) maltodextrin.

As used herein, the term "a" or "an" of an entity refers to one or more of that entity; for example, a buffer refers to one or more buffers or at least one buffer. As such, the terms "a", "an", "one or more", or "at least one" can be used interchangeably.

As used herein, "*Lactobacillus* species" refers to an isolated strain of the genus *Lactobacillus* having identifying characteristics that render the species suitable for use with the present invention. Exemplary non-limiting identifying characteristics can include a specified percent vaginal epithelial cell (VEC) cohesion value, ability to produce $H_2O_2$, ability to produce lactic acid, genetic stability over time both in vivo and in vitro, and a relatively large size. A particular strain suitable for use with the present invention can exhibit one or more identifying characteristics. Non-limiting exemplary values for each of these identifying characteristics are disclosed herein.

As used herein the term "isolated strain" refers to a bacterial strain that has been removed from its natural milieu. The term "isolated" does not necessarily reflect the extent to which the microbe has been purified. In contrast, the phrase "substantially pure culture" refers to a microbial culture that contains substantially no other microbes other than the desired strain or strains, and substantially free of other contaminants, which can include microbial contaminants as well as unwanted chemical contaminants.

As used herein the term "buffer" or "buffering agent" refers to the active component of a buffering solution, which when placed into solution dissociates into a weak acid and its conjugate base. The buffer or buffering agents, when placed in solution resist change in pH when $H^+$ or $OH^-$ is added. A buffer can be a single compound, e.g., arginine, a phosphate salt, $Na_2HPO_4$, $NaHCO_3$, or a combination of compounds where the buffer or buffering agents has a $pk_a$ of at least 4.3.

As used herein the phrase "dried *Lactobacillus* preparation" or "dried microbial preparation" refers to a preparation of *Lactobacillus* (or other microbial genus suitable for use with the invention) that does not contain at least one buffering agent having a $pk_a$ of at least 4.3, wherein 140 mg of the dried *Lactobacillus* preparation in 3 ml of water does not maintain a pH of at least 4.3 with the addition of 60 µl of 0.1N HCl.

As used herein, the term "dried formulation" or "vaginal medicant" refers to a preparation of live *Lactobacillus* (or other microorganism) that contains less than 5% moisture, is suitable for long-term storage, and has at least one buffering agent having a $pk_a$ of at least 4.3, wherein 140 mg of the dried *Lactobacillus* preparation in 3 ml of water is capable of maintaining a pH of at least 4.3 with the addition of 60 µl of 0.1N HCl. The moisture content in a dried formulation is determined gravimetrically after drying at 105° C. for 24 hours.

As used herein the term "preservation formulation" or "preservation matrix" refers to a composition capable of preserving and maintaining a bacterial cell culture in a metabolically inactive state while minimizing the damaging effects encountered during the preservation process. A preservation matrix as used herein typically includes a biologically active binding agent, an anti-oxidant, a polyol, a carbohydrate, and/or a proteinaceous material. The preservation matrix is capable of maintaining at least $10^6$ viable, genetically stable cells for a period of at least 12 months in vitro.

As used herein the term "rehydrating" refers to the process of restoring a dried microbial formulation or preparation from a metabolically inactive state to a metabolically active state. Rehydration can be carried out in vitro, or in vivo.

As used herein, the term "colonizing" refers to the establishment of a site of microbial reproduction on a cell or material with does not necessarily result in tissue invasion or damage. In vitro, colonization can be quantified by counting the number of colony forming units (CFU)/ml when grown on suitable bacterial agar plates as described herein and known in the art.

As used herein "contacting" or "administering" refers to a method for applying a dried microbial formulation of the present invention to a site on a vaginal wall, where the rehydrated microorganisms will colonize.

As used herein, "therapeutically effective amount" refers to that amount of a dried microbial formulation of the present invention that leads to the desired therapeutic effect. The desired therapeutic effect is prophylaxis and/or treatment of infections of the urogenital tract, such as bacterial vaginosis or any other bacterial disorder in the vagina.

II. Introduction

The present invention is based in part on the surprising finding that adding at least one buffering agent to a microbial preparation (either before or after drying) has a dramatic effect on the stability of the bacteria during preservation and allows for maximal recovery of live bacteria following rehydration in an acidic environment. Specifically, as disclosed herein, the present invention provides methods and compositions for *Lactobacillus* Replacement Therapy (LRT) to repopulate the vaginal mucosa with desirable *Lactobacillus* microflora as a way to maintain good vaginal health. As described in more detail below, the present invention teaches methods, compositions, and reagents for the preparation and use of transiently buffered dried *Lactobacillus* formulations.

III. Suitable *Lactobacillus* Species

Bacterial cultures suitable for use with the present invention include substantially pure bacterial cultures of an isolated bacterial strain that posses one or more of the identifiable characteristics as described in more detail below. In some embodiments, the bacterial cultures are of an isolated strain of the genus *Lactobacillus*.

A *Lactobacillus* strain suitable for use in the present invention can be any *Lactobacillus* strain that exhibits at least one identifiable characteristic as described herein. *Lactobacillus* strains can be detected and isolated from natural sources through the use of appropriate screening techniques known in the art. In some embodiments, a *Lactobacillus* strain suitable for use with the invention is isolated from the vagina of a human. The identifying characteristics of *Lactobacillus* strains suitable for use in the present invention and methods to screen for these characteristics are discussed in detail below. Non-limiting exemplary bacterial strains suitable for use with the instant invention include *L. gasseri, L. casei, L. rhamnosus, L. acidophilus, L. fermentum, L. johnsonii, L. vaginalis, L. gallinarum, L. coleohominis, L. jensenii, L. iners,* and *L. crispatus*. Additional bacterial species suitable for use with the present invention are well known to persons of skill in the art, as disclosed in, for example, U.S. Pat. Nos. 7,312,067 and 6,468,526.

It is within the scope of the present invention that, in addition to known species and strains of *Lactobacillus*, newly identified species and strains from nature and mutant strains derived from known or newly identified strains can be used in the present invention. Mutants of a parental strain of *Lactobacillus* that an identifiable characteristic suitable for use with the present invention can be isolated from natural sources, induced by exposure of a parental strain to a mutagen, or obtained by genetic engineering. Mutant strains suitable for use with the present invention typically is a mutated parental microorganism in which the nucleotide composition of such microorganism has been modified by a mutation(s) resulting in an improvement of one or more identifiable characteristics as described herein.

In some embodiments, a single bacterial strain is used in preparing the dried formulations. In some embodiments a combination or two or more bacterial strains are combined in the dried formulation.

One identifying characteristic of a *Lactobacillus* suitable for use in the present invention is that the *Lactobacillus* strain has a percent vaginal epithelial cell (VEC) cohesion value of at least about 50%. A "percent VEC cohesion value" is defined as the percentage of VECs to which at least one *Lactobacillus* cell is adhered in the total number of VECs in an identified group. In some embodiments, the VEC value is 60%, 70%, 80%, 85%, 90%, 95% or higher. According to the present invention, the terms "cohesion" and "adherence" can be used interchangeably. Adherence of microbial cells to vaginal epithelial cells is critical for colonization and biological effect. Successful adherence of a *Lactobacillus* cell of the present invention to a vaginal epithelial cell results in successful colonization of the vaginal epithelial cell. Long term in vivo colonization is a goal of the products and methods of the present invention, and "percent VEC cohesion value" is a good predictor of whether a significant number of VECs will accept microbial cells in vitro and in vivo. See, U.S. Pat. No. 6,468,526. In some embodiments, an isolated *Lactobacillus* strain suitable for use in the present invention is identified by its ability to sustain colonization of vaginal epithelial cells for at least about 1 month.

Another identifying characteristic of a *Lactobacillus* suitable for use in the present invention is the ability to produce hydrogen peroxide ($H_2O_2$). Hydrogen peroxide has been shown to be directly responsible for the killing of other microorganisms by *Lactobacillus*. In some embodiments, the *Lactobacillus* species can produce greater than about 0.5 ppm of $H_2O_2$ under normal growth conditions. In some embodiments, *Lactobacillus* species can produce at least about 10 ppm to about at least about 20 ppm or more of $H_2O_2$ under effective growth conditions, which include any medium and conditions capable of promoting the production of $H_2O_2$. Effective growth conditions include both in vitro growth conditions (e.g., an effective culture medium and conditions) and in vivo growth conditions (e.g., successful rehydration and colonization of a vaginal epithelial cell).

The production of $H_2O_2$ by a *Lactobacillus* species of the present invention can be quantitated by any means known in the art for measuring $H_2O_2$ production. For example, $H_2O_2$ production can be measured by spectrophotometric quantitation of a blue pigment formed when *Lactobacillus* is inoculated onto tetramethylbenzidine medium (TMB) and incubated under anaerobic conditions. $H_2O_2$ production can also be measured using commercially available $H_2O_2$ detection strips (e.g., available from EM Sciences).

Another identifying characteristic of a *Lactobacillus* suitable for use in the present invention is the genetic stability of the *Lactobacillus* over time both in vivo and in vitro. Genetic stability refers to the ability of successive generations of a *Lactobacillus* strain to substantially maintain the genetic profile of the mother strain, and not acquire substantial mutations in its DNA over time related to one or more of the identifiable characteristics described herein. In other words, successive generations of a genetically stable strain will not acquire substantial mutations (e.g., mutations that significantly change the phenotype of the encoded protein) in DNA related to the identifying characteristics of vaginal epithelial cell cohesion value, hydrogen peroxide production, or the ability to adhere to vaginal epithelial cells in a metabolically inactive state as described herein. In some embodiments, a *Lactobacillus* strain of the present invention which has colonized vaginal epithelial cells in vivo will maintain genetic stability in vivo for at least about 12 months of vaginal colonization. In some embodiments, a *Lactobacillus* strain of the present invention which has colonized vaginal epithelial cells in vivo will maintain genetic stability in vivo for at least about 18 months to about 24 months of vaginal colonization. In vitro, the genetic stability of a microorganism can be affected by the culturing conditions of the microorganism and by the preparation and storage format of the dried *Lactobacillus* formulation. Genetic stability can be evaluated by any method of evaluating mutations or identifying selectable genetic markers known in the art. For example, genetic marker profiles based on restriction endonuclease patterns can be performed to establish the stability of a genetic profile for a particular culture compared to the mother strain. In some embodiments, Polymerase Chain Reaction (PCR) can be used to distinguish as many as 40 different strains of *Lactobacillus* from each other, and to confirm the genetic stability of a particular strain of *Lactobacillus* over time after either in vitro storage or in vivo colonization of vaginal epithelial cells.

In some embodiments, an identifying characteristic of a microbial species suitable for use in the present invention is the ability to produce lactic acid. Lactic acid has been shown to inhibit the growth of pathogens in vitro. In some embodiments, a microbial species suitable for use in the present invention produces at least about 0.75 mg lactic acid/100 ml. In some embodiments, a microbial species suitable for use in the present invention produces at least about 4 mg lactic acid/100 ml culture to at least about 8.8 mg lactic acid/100 ml culture under effective growth conditions.

In some embodiments of the present invention, a suitable microbial strain has a relatively large cell size. The large cell size provides for better bio-competitive exclusion, which is the ability of the desired bacterial strain or strains to competitively inhibit the growth of undesired bacterial strains. Such exclusion is attributed to the occupation of available space on a vaginal epithelial cell by the beneficial microbial cells, thus preventing attachment of pathogenic, or undesirable, microbial cells. Typical ranges of cell size for *Lactobacillus* provided in Bergey's Manual of Determinative Bacteriology are about 0.8-1.6 μm (width)×2.3-11 μm (length). In some embodiments, a microbial strain suitable for use in the present invention has a cell size of from about 1 to about 2 μm in width and from about 2 to about 4 μm in length.

An isolated bacterial strain of the genus *Lactobacillus* suitable for use with the present invention can have one or more of the desirable identifying characteristics described herein. For example, in some embodiments, an isolated bacterial strain of the genus *Lactobacillus* is able to sustain colonization of vaginal epithelial cells for at least about 1 month. In some embodiments, an isolated bacterial strain of the genus *Lactobacillus* maintains genetic stability over a period of at least about 24 months of vaginal colonization. In yet another embodiment, such a strain adheres to vaginal epithelial cells when the strain is in a metabolically inactive state (i.e., when in a preserved state). In some embodiments, such a strain can produce at least about 0.75 mg lactic acid/100 ml culture under effective growth conditions. In some embodiments, such a strain is from about 1 micron to about 2 microns in width and from about 2 microns to about 4 microns in length. Additional identifiable characteristics, desirable of a *Lactobacillus* species suitable for use with the present invention will be well known to persons of skill in the art.

IV. Preparation of the Dried Formulation

In preparing a dried *Lactobacillus* formulation of the present invention, a suitable *Lactobacillus* species, as described above, is selected, and then grown to a biomass and processed as described below.

A. Fermentation

*Lactobacillus* suitable for use with the present invention can be cultured by any suitable means known in the art. Any culture medium that provides for the effective growth of the selected microorganism without contamination, loss of genetic stability, or loss of any other desirable identifying and functional characteristics can be used with the present invention. Generally, the microorganisms are grown to log phase in a suitable nutrient media. Non-limiting exemplary nutrient media suitable for use in culturing microorganisms for use with the present invention include, MRS broth, Rogosa broth, Thayer-Martin media, Trypticase Soy, Brain-Heart infusion broth, or any other enriched media free of animal sources suitable for the cultivation of the selected microorganism. In some embodiments, additional solutions may be added to the nutrient broth, for example a base control solution can be used to control the pH of the culture, and/or a glucose control solution can be used to control the level of glucose throughout the culture period. A person of ordinary skill in the art will know of many such media, and will be able to select a suitable media for cultivation of a particular microorganism without undue experimentation.

The microorganisms for use with the present invention can be cultured using any conventional culture methodology known in the art. Non-limiting exemplary culture methods include agar surface culture, batch culture, broth fermentation, and the use of large scale bioreactors.

In some embodiments, the selected microorganism is cultured using a modified draw and feed strategy as detailed in Example 1. Basically this strategy involves an initial fed batch fermentation, followed by removal of a portion of the contents of the bioreactor and replacement of that portion with fresh sterile broth. The pH of the fermentation broth can be maintained within a desired range by the addition a suitable base. In some embodiments, the pH of the fermentation is maintained in the range from about 5.0 to about 8.0 with the addition of ammonium hydroxide, sodium hydroxide, or potassium hydroxide. The pH to be maintained and the agent used to maintain the pH will depend on the particular species being cultured and other parameters surrounding the fermentation process, as are well known to persons of skill in the art. Example 1 details the fermentation parameters for *L. jensenii* 1153 fermented with an MRS broth at pH 6.0 using a 90% draw/10% feed strategy.

In some embodiments, the temperature of the culture medium can be any temperature suitable for growth of the selected microorganisms. For example, prior to inoculation of the culture medium with an inoculum, the culture medium can be brought to and maintained at a temperature in the range of from about 20° C. to about 35° C.

The culture medium is inoculated with an actively growing culture of the selected microorganism in an amount sufficient to produce, after a reasonable growth period, a suitable cell density for further processing and drying. In some embodiments, inoculation cell densities are within the range of from about $10^6$ CFUs/ml to about $10^9$ CFUs/ml. The cells are then grown to a cell density in the range of about $10^7$ CFUs/ml to about $10^{11}$ CFUs/ml. In some embodiments, the cell density is in the range of about $10^8$ to about $10^{10}$ CFUs/ml at the time of harvest. At this stage, the cells are harvested for further processing with the preservation matrix. It is to be understood that one of ordinary skill in the art will appreciate variations to the basic culturing, harvesting and processing steps disclosed herein and as such, the present invention incorporates such variations.

B. Processing the Bacterial Biomass

After reaching the desired cell density, the microbial cells are harvested using any suitable method known in the art to remove the cells from the culture media. Non-limiting exemplary methods for harvesting the cultured cells includes, filtration, centrifugation, and sedimentation. In some embodiments, the cell biomass is washed at least once using a physiologically balanced salt solution. In some embodiments, the wash solution may contain additional components, such as glucose. In some embodiments, the wash solution comprises a buffer or one or more buffering agents. Non-limiting exemplary buffering agents that may be used or added to the wash solution include phosphate salts, $Na_2HPO_4$, $NaHCO_3$, and arginine.

After separation of the cells from the culture media and/or washing of the biomass, the cells are centrifuged to form a cell paste in preparation for suspension in a preservation matrix. In some embodiments, the cell paste is resuspended and washed using a phosphate buffer, or other physiologically suitable buffer as known to persons of skill in the art. In some embodiments, the cell paste is diluted in a phosphate buffer or other physiologically suitable buffer. The washed and/or diluted cell paste is then suspended in a preservation matrix.

1. Preservation Matrix

The preservation matrix is comprised of ingredients to minimize the damaging effects encountered during the preservation process and to provide functional properties. A suitable preservation matrix for use with the present invention can be any preservation matrix known in the art. The particular preservation matrix will depend on the particular bacterial species and the type of drying process used. For example, if the bacterial preparation is to be freeze dried, then the preservation matrix will include components known to protect against cryo-damage, such as trehalose or sucrose solutions. An exemplary preservation matrix suitable for use with the present invention is disclosed in U.S. Pat. No. 6,372,209. Other preservation matrices suitable for use with the present invention are known to persons of skill in the art as disclosed in U.S. Pat. Nos. 5,614,209; 7,122,370; and 6,610,531. A preservation matrix suitable for use with the present invention is able to maintain genetically stable microorganisms for at least 12 months in vitro. Additional drying methodologies and protective agents are disclosed in the review by Morgan et al. (2006) J. Microbiol. Meth. 66:183-193.

In some embodiments, the preservation matrix acts to convert the cultured microorganisms from an actively growing metabolic state to a metabolically inactive state. A preservation matrix suitable for use with the present invention is formulated for optimal microbial cell resilience, such that upon rehydration in vivo, the microbial cells are immediately free to adhere to vaginal epithelial cells and then return to full metabolic activity.

In some embodiments, the preservation matrix includes a biologically active binding agent, an antioxidant, a polyol, a carbohydrate and a proteinaceous material. A biologically acceptable binding agent is any physiologically acceptable agent (e.g., does not have any biological activity or toxic effect in vivo) that affixes the cell matrix to an inert carrier during the preservative process and which provides protective effects (i.e., maintains cell viability) throughout preservation and storage of the microbial cells. Non-limiting exemplary biologically acceptable binding agents suitable for use with the present invention include water-soluble gum, carboxymethyl cellulose and/or gelatin. In some embodiments, the biologically acceptable binding agent comprises from about 10% to about 20% by weight of the preservation matrix. In some embodiments, a preservation matrix comprises about 14% gelatin by weight of the preservation matrix.

In some embodiments, the preservation matrix comprises an antioxidant to retard oxidative damage to the microbial cells during the preservation and storage process. Non-limiting exemplary antioxidants suitable for use with the instant invention include sodium ascorbate and vitamin E (α-tocopherol). In some embodiments, the antioxidant comprises from about 0.1% to about 1.0% by weight of the preservation matrix. In some embodiments, a preservation matrix comprises about 0.5% sodium ascorbate by weight of the preservation matrix.

In some embodiments, the preservation matrix comprises a polyol (i.e., polyhydric alcohol) to maintain the native, uncollapsed state of cellular proteins and membranes during the preservation and storage process. Non-limiting exemplary polyols suitable for use with the present invention include xylitol, adonitol, glycerol, dulcitol, inositol, mannitol, sorbitol and/or arabitol. In some embodiments, the preservation matrix comprises from about 1% to about 12% polyol by weight of the preservation matrix. In some embodiments, the preservation matrix comprises about 6% xylitol by weight of the preservation matrix.

In some embodiments, the preservation matrix comprises a carbohydrate to maintain the native, uncollapsed state of cellular proteins and membranes during the preservation and storage process. Non-limiting exemplary carbohydrates suitable for use with the invention include dextrose, lactose, maltose, sucrose, fructose and/or any other monosaccharide, disaccharide or polysaccharide. In some embodiments, the preservation matrix comprises from about 0.5% to about 12% carbohydrate by weight of the preservation matrix. In some embodiments, the preservation matrix comprises about 2.5% dextrose by weight of the preservation matrix.

In some embodiments, the preservation matrix comprises a proteinaceous material to protect the microbial cell during the dehydration portion of the preservation process. Non-limiting exemplary proteinaceous materials suitable for use with the invention include skim milk and albumin. In some embodiments, the preservation matrix comprises from about 0.5% to about 5% proteinaceous material by weight of the preservation matrix. In some embodiments, the preservation matrix comprises about 1.5% skim milk by weight of the preservation matrix.

In some embodiments, a preservation matrix suitable for use with the present invention includes a biologically active binding agent that is at least about 10% of the preservation matrix by weight, an antioxidant that is at least about 0.1% of the preservation matrix by weight, a polyol that is at least about 1% of the preservation matrix by weight, a carbohydrate that is at least about 0.5% of the preservation matrix by weight, and a proteinaceous material that is at least about 0.5% of the preservation matrix by weight.

In some embodiments, a preservation matrix suitable for use with the present invention comprises about 14% gelatin, about 0.5% sodium ascorbate, 0.1% vitamin E (α-tocopherol) about 2.5% dextrose, about 1.5% skim milk and about 6% xylitol, by weight of the preservation matrix.

2. Buffering Agents

The present inventors have surprisingly discovered that adding at least one buffering agent to the bacterial preparation greatly enhances the stability and recovery of the bacteria following rehydration in an acidic environment. In some embodiments, the cells are washed with a buffer after removal from the culture medium and before suspension in a preservation matrix as discussed above. In some embodiments, the buffering agent(s) can be added to the cell paste prior to suspension in the preservation matrix. In some embodiments, the buffering agent is added to the preservation matrix. In some embodiments, the buffering agent can be added to a dried bacterial preparation that does not yet comprise a buffering agent, or does not comprise sufficient buffering agent as determined using functional tests described herein.

A buffering agent suitable for use with the present invention is a physiological agent, i.e., does not exert any toxic effects on the cultured microorganisms, vaginal epithelial cells, or a female patient using the dried formulation. In some embodiments, the buffering agent has a $pk_a$ of at least 4.2. In some embodiments, the buffering agent has a $pk_a$ of at least 4.3, 4.4, 4.5, 4.6, 4.7, 4.8, 4.9, 5.0, 5.5, 6.0, 6.5, 7.0, 7.5, 8.0, or higher. In some embodiments, the buffering agent has a $pk_a$ of at least 4.3. In some embodiments more than one buffering agent is used where each buffering agent has a different $pk_a$. Non-limiting exemplary buffering agents suitable for use with the present invention include $Na_2HPO_4$, $NaHCO_3$, phosphate salts, and arginine. In some embodiments, the buffering agent is present in a concentration range from about 6.25 mM to about 800 mM. In some embodiments the lower limit of the concentration range is about 6.25 mM, 10 mM, 12.5 mM, 15 mM, 20 mM, 25 mM, 30 mM, 40 mM, 50 mM, 75 mM, 100 mM, 125 mM, 150 mM, 175 mM, 200 mM, 250 mM, 300 mM, 400 mM, 500 mM, 600 mM, or 700 mM. In some embodiments, the upper limit of the concentration range is about 10 mM, 12.5 mM, 15 mM, 20 mM, 25 mM, 30 mM, 40 mM, 50 mM, 75 mM, 100 mM, 125 mM, 150 mM, 175 mM, 200 mM, 250 mM, 300 mM, 400 mM, 500 mM, 600 mM, 700 mM, or 800 mM. In some embodiments, a buffering agent is present in a concentration of about 6.25 mM, 10 mM, 12.5 mM, 15 mM, 20 mM, 25 mM, 30 mM, 40 mM, 50 mM, 75 mM, 100 mM, 125 mM, 150 mM, 175 mM, 200 mM, 250 mM, 300 mM, 400 mM, 500 mM, 600 mM, 700 mM, or 800 mM. In some embodiments the buffering agent is present in a concentration range from about 10 mM to about 200 mM. In some embodiments the buffering agent is present in a concentration range from about 25 mM to about 200 mM.

A buffered dried bacterial formulation of the present invention is able to preserve the viability of a genetically stable isolated bacterial strain suitable for use with the present invention for at least about 12 to about 24 months in vitro during storage at room temperature or at refrigeration temperature (2-8° C.).

a) Assay for Testing the Buffering Capacity of the Dried Formulation

For general purposes, to determine if a sufficient amount of buffering agent has been added to a bacterial formulation as described herein, a skilled artisan can use any suitable physical or physiological test known in the art. Non-limiting exemplary tests can include acid titration of a specific amount of the dried formulation, rehydration in an acidic environment (e.g., synthetic vaginal fluid (SVF) based on the formulation of Moosa et al. (2004) followed by plating on bacterial agar plates to determine survival (see, Example 2), or in vivo testing using animal models to demonstrate successful colonization. A skilled artisan will know of additional methods for determining if a particular dried bacterial formulation falls within the scope of the present invention.

For purposes of this invention, a simple acid titration test can be conducted on a dried formulation of the invention to determine if the dried formulation comprises sufficient buffering capacity. In some embodiments, a dried bacterial formulation comprising sufficient buffering agent is one where 140 mg of a dried bacterial formulation rehydrated in 3 ml of sterile water maintains a pH above 4.3 upon the addition of 60 μl of 0.1N HCl. In some embodiments, the pH of the solution will remain above 4.4, 4.5, 4.6, 4.7, 4.8, 4.9, 5.0, 5.2, 5.4, 5.6, 5.8, 6.0, 6.5, 7.0, 7.5, 8.0 or higher upon the addition of 60 μl of 0.1 N HCl. In some embodiments, a preservation matrix is optimized before being used to prepare bacterial formulations of the present invention. For example, a preservation matrix can be dried without bacteria, tested, remixed to add or change the concentration of buffering agents, and then re-tested, etc. When the preservation matrix maintains the desired pH upon addition of the acid, the formulation can be used in the preservation of bacteria as described herein. Such testing and optimization is well within the skill of a person of ordinary skill in the art without undue experimentation.

3. The Bacterial Formulation

The desired bacterial cells, combined with the preservation matrix comprising at least one buffering agent as described above comprises the bacterial formulation of the present invention.

Another aspect of the present invention relates to a method for making the bacterial formulation as described herein. In some embodiments, the method includes the steps of (a) providing components which include: (i) a sterile biologically active binding agent, which can include water soluble gum, carboxymethyl cellulose or gelatin; (ii) a sterile proteinaceous material which can include skim milk or albumin; (iii) a sterile polyol which can include xylitol, adonitol, glycerol, dulcitol, inositol, mannitol, sorbitol or arabitol; (iv) at least one sterile antioxidant; (v) a sterile carbohydrate which can include dextrose, lactose, maltose, sucrose, fructose, and other monosaccharides, other disaccharides and other oligosaccharides; (vi) at least one buffering agent having a $pk_a$ of at least 4.3, which can include, phosphate salts, $NaHCO_3$, $Na_2HPO_4$, and/or arginine; and (vii) water; and (b) and mixing said components together to form a solution. The biologically active binding agent is provided in a liquid form, which typically requires heating of the agent to about 37° C., since such agents are likely to be in solid phase at room temperature. The components of the preservation matrix can be sterilized by any suitable method of sterilization. In some embodiments, the biologically active binding agent, buffering agent(s) and the proteinaceous material are sterilized by autoclave and the polyol, carbohydrate and antioxidant are sterilized by filtration. After the components are mixed the preservation matrix solution can either be used immediately, held at 37° C. for short periods of time, or frozen for longer periods of time at about −20° C.

In some embodiments, the dried bacterial formulation of the present invention (i.e. a vaginal medicant) includes an inert carrier. According to the present invention, an inert carrier can be any inert material which is suitable for use in vivo and which can be used to carry or support the cell suspension matrix (i.e., preservation matrix combined with microbial cells) of the present invention in such a manner that the cell suspension matrix can be stored in vitro and/or administered in vivo. Non-limiting exemplary inert carriers suitable for use with the invention can include maltodextrin beads and gelatin capsules. Such carriers are discussed in more detail below.

The ability of the formulation to preserve a minimum number of viable cells is critical to the efficacy of the vaginal medicant and has been particularly problematic in vaginal treatments prior to the present invention. More specifically, the number of viable, substantially pure, genetically stable cells that are delivered in a single dose (e.g., a single suppository or tablet) is directly related to the critical issue of potency of the dried formulation. As used herein, the term "efficacy" refers to the ability of a suppository strain to exhibit a biological effect (e.g., provide a statistically significant level of protection against vaginal infection). "Potency" relates directly to the number of viable microbial cells delivered per dose (i.e., per suppository or tablet). According to the present invention, viable cells have the ability to grow and reproduce. For a dried microbial formulation of the present invention to be efficacious in vivo, both colonization of the vaginal epithelial cells by the microbial cells at a potency of at least about $10^6$ and a biological effect (e.g., alleviation or prevention of an infected state such as bacterial vaginosis, urinary tract infection, and yeast vaginitis) are necessary. There is a difference between the potency of a formulation that allows colonization of the suppository strain and the potency of a formulation that provides a biological effect. The ability of a dried bacterial formulation of the invention to colonize vaginal epithelial cells combined with the specific potency requirements for a biological effect are critical for an efficacious vaginal medicant as in the present invention. More specifically, a concentration of viable microbial cells that results in vaginal colonization of a dried microbial formulation of the present invention is necessary, but may not be sufficient, for the dried formulation to be efficacious. For example, colonization of vaginal epithelial cells can be achieved at very low potencies (e.g., $10^5$ microbial cells) using the *Lactobacillus* strains and preservation format that does not include at least one buffering agent as described herein. However, biological effect is not demonstrated at this potency. Therefore, colonization of vaginal epithelial cells is necessary for a biological effect, but colonization in the absence of insufficient potencies will not lead to the numerical superiority necessary to demonstrate biologic effect. The dried formulation of the present invention demonstrates a surprising ability to maintain the necessary potency of biologically effective *Lactobacillus* cells both in vitro over extended periods of time and in vivo upon delivery to vaginal epithelial cells.

In some embodiments of the present invention, more than one microbial species is included in a single dried formulation. In these embodiments each microbial strain is selected for its ability to prevent and/or treat a vaginal infection which is different from the vaginal infection prevented or treated by the other microbial strains included in the medicant. Such infections can include, but are not limited to, bacterial vaginosis, symptomatic yeast vaginitis, gonorrhea, chlamydia, trichomoniasis, human immunodeficiency virus infection, urinary tract infection, and pelvic inflammatory disease. For example, in some embodiments, a vaginal medicant includes a first *Lactobacillus* strain which is useful for preventing bacterial vaginosis, and a second *Lactobacillus* strain which is useful for preventing symptomatic yeast vaginitis. In some embodiments, a first *Lactobacillus* strain is a strain of *L. crispatus* and a second *Lactobacillus* strain is a strain of *L. jensenii*. In some embodiments, a first *Lactobacillus* strain is a strain of *L. crispstus* and a second *Lactobacillus* strain is a strain of *L. jensenii*, and a third *Lactobacillus* strain is a strain of *L. gasseri*. In some embodiments, at least one strain of the same *Lactobacillus* species is used.

One embodiment of the present invention relates to a method to preserve microbial cells within a preservation matrix to form a vaginal medicant. This method includes the steps of (a) suspending a culture of at least about $10^6$ microbial cells in a preservation matrix which includes a biologically active binding agent, an antioxidant, a polyol, a carbohydrate, and a proteinaceous material, to form a cell matrix suspension; (b) adding the cell matrix suspension to an inert carrier to form a delivery composition; and removing water from the delivery composition.

In some embodiments, the preservation matrix can comprise a rehydration formulation to facilitate the rehydration and recovery of the bacteria. Non-limiting exemplary components of a rehydration formulation can include glucose, potassium citrate, sodium chloride, and sodium citrate. In some embodiments, the preservation matrix can include thickening agents, such as corn starch, guar gum, xantham gum, and the like. In some embodiments, the preservation matrix may also include preservatives, for example, methylparaben, propylparaben, benzyl alcohol, and ethylene tetraacetate salts. In some embodiments, the preservation matrix can include a plasticizer such as glycerol or polyethylene glycol. Additional formulations and components are well known in the art as described in for example, PCT Int'l. Pub. No. WO 2005/034861.

4. Drying and Packaging of the Bacterial Formulation

The final step in preparing a vaginal medicant of the present invention is drying the formulation. Numerous methods are known in the art for drying a bacterial preparation to increase their stability for long term storage. Typically the effect of drying is to place the bacteria in a state of dormancy to protect the bacteria from environmental elements that negatively impact the viability of the bacteria. The standard way to bring about dormancy is through the removal of water. Organisms differ in their initial water content as well as the amount of water that must be removed in order to induce a dormant state. The essential goal is to remove sufficient water that the normal cellular (e.g. enzymatic activity) processes come to a halt or are at least greatly diminished. A dried formulation of the present invention has less than about 5% moisture content.

There are three types of water in microorganisms: Free water, bound water, and preserved water. Free water is intercellular water and a part of the intracellular water. When free water is evaporated the drying rate slows. Bound water is that fraction of the intracellular water that combines with proteins, nucleic acids, membranes, and other cellular material. The drying rate decreases further as bound water is removed, and reaches a plateau when most of the bound water has been removed. Preserved water is isolated in lipid pockets and other membrane components and is highly resistant to drying. The stability of a microorganism increases when the free water has been removed. Generally, this represents a range of 20-25% moisture content. Dormancy is typically achieved when most of the free water and the bound water are removed. In most drying processes, energy is added to the system to remove the water. When energy is added without a decrease in water content, this is an indication that most of the bound water has been removed and only preserved water remains. The correct level of water removal can typically be judged by assessing the water content of the cell during the drying process. In general, water content will decrease to the point where free and bound water are largely removed. This point is reflected as a plateau when water content is plotted against drying time on a graph. In some embodiments, this plateau occurs when water content is reduced to about 10% or less.

In some embodiments, the water content of the dried formulation is about 5%. In some embodiments, the water content of the dried formulation is less than about 5%, 4%, 3%, 2%, 1%, or less. Water content in a *Lactobacillus* powder can be determined gravimetrically after drying at 105° C. for 24 hours. Alternatively, an instrument for measuring water content in powders could be used to monitor the moisture content of the formulation during drying, e.g., the IR-120 Moisture Analyzer (Denver Instruments, Denver, Colo.). Water content in a *Lactobacillus* powder could also be measured as water activity (Aw) using a water activity meter, e.g., a Decagon AquaLab Model series (Decagon Instruments, Pullman, Wash.), or a Rotronic Model series (Rotronic Instrument Corp., Huntington, N.Y.). A person of skill in the art will know of other suitable devices that can be used to monitor the water content of the formulations in the present invention.

Numerous methods are known in the art for drying bacterial preparations. See, e.g., Morgan et al. (2006) *J. Microbiol. Meth.* 66:183-193. Non-limiting exemplary drying methods suitable for use with the present invention include air drying, vacuum drying, oven drying, spray drying, flash drying, fluid bed drying, controlled atmosphere drying, and freeze drying. In some embodiments, a desiccant is used to aid in the drying process, and/or to prevent resorbtion of moisture into the dried formulation. In some embodiments, the drying is carried out using a fluid bed dryer. In some embodiments, the drying is carried out using a spray dryer. In some embodiments, the drying temperature is in the range from about 40° C. to about 140° C. In some embodiments, the drying temperature is in a range from about −70° C. to about 30° C. In some embodiments, the relative humidity of the air flow is in the range from about 30% to 0%.

In some embodiments, the cells suspended in preservation matrix are spray-dried onto a maltose dextrin seed in a 300N fluid bed drier (Applied Chemical Technology, Inc.). In some embodiments, a Buchi Mini spray drier B-290 (Buchi Laboratory Equip. Zurich Switzerland) is used. In some embodiments, a VirTis AdVantage Freeze Dryer (SP Industries, Inc.) is used. In some embodiments, the maltose dextrin accounts for approximately 70% of the dried powder.

Conventional methods of preserving microbial cells commonly employ air drying, spray drying or freeze drying. Air drying requires long periods of time, sometimes with somewhat elevated temperatures. Spray drying exposes the cells to hot air, turbulence and excessive levels of oxygen. Freeze drying requires dramatic fluctuations in temperature and the inherent risk of ice crystal formation. An advantage of the formulation of the present invention is that the preservation matrix allows removal of water from the cells by a variety of conventional drying methods with minimal damage to the microbial cells. In some embodiments, the method of producing the vaginal medicant of the present invention encompasses processing steps which are most likely to reduce stress to the cells during harvest, dispensing and preservation so as to maximize the likelihood of a final product with long shelf-life and capability of delivering viable cells of the bacterial strain having the desirable characteristics described herein. Stresses to avoid can include an excessive number of processing steps, dramatic fluctuations of temperature or pressure, exposure to moisture and long processing times. The process preferably limits the introduction of contaminating microorganisms, a common problem in existing commercial preparations of Lactobacillus.

In some embodiments, the formulation is coated onto an inert carrier, e.g., a maltodextrin bead. The coated beads are then dried, e.g., by a fluid bed drying method. Fluid bed drying methods are well known in the art. In some embodiments, maltodextrin beads are placed into a fluid bed dryer and dried at 33° C. The air pressure is set to 14 psi, the formulation is sprayed onto the beads and the temperature is increased to 38° C. The coated beads are then allowed to dry for an additional period of time, until the desired amount of water has been removed. The dried coated maltodextrin beads can be stored as a powder, placed into gelatin capsules, or pressed into tablets.

In some embodiments of the present invention, a suppository format comprising a gelatin capsule is used for delivering bacterial cells of the vaginal medicant in an exogenous fashion to the vaginal milieu. Gelatin capsules are commercially available and are well known in the art. In some embodiments, the bacterial cells suspended in the preservation matrix comprising at least one buffering agent as described herein is dispensed into a gelatin capsule, which is then chilled until the cell suspension matrix forms a non-fluid matrix affixed to the interior wall of the gelatin capsule, and then desiccating the gelatin capsule in a desiccation chamber. The step of dispensing can be accomplished by any means known in the art, including manual, semi-automated and automated mechanisms. The chilling step is performed at from about 4° C. to about 6° C. The step of desiccating the gelatin capsule can include the steps of (i) providing dry air to the desiccation chamber containing less than about 25% moisture, at a temperature from about 24° C. to about 32° C.; and (ii) removing humidified air from the desiccation chamber.

In embodiments employing the use of a gelatin capsule, the desiccation process can proceed for about 1 to about 6 hours. The desiccation chamber can include a compressor, at least one hydrocarbon scrubbing filter and a chilled air compressor with or without a desiccant silica gel (or any other suitable desiccant material) column, in series. In some embodiments, the air entering the chamber (dry air) contains less than about 25% moisture. In some embodiments the air entering the chamber contains less than 15%, 10%, 5%, down to as little as zero moisture. In some embodiments, the dry air entering the chamber has a temperature between about 24° C. to about 32° C. In some embodiments, the rate of airflow is about 2 air exchanges per minute. This method allows for the improved preservation of microbial cells in a controlled environment with room temperature air in a short period of time.

In some embodiments, the delivery compositions are placed into a package to protect against moisture and oxygen during transport and storage. The package can be comprised of any suitable material for such protection such as Mylar or metallic film pouches. In some embodiments, the delivery compositions are sealed into individual packages. In other embodiments, a single package may comprise multiple cavities. In some embodiments, a package with multiple cavities can comprise the same or different doses of the composition as discussed below.

V. Dosing and Method of Administration

The dried formulations of the present invention are useful in *Lactobacillus* Replacement Therapy (LRT). Dosing of the dried *Lactobacillus* formulation is dependent on multiple factors well known to a person of skill in the art. Typical factors may include, but are not limited to the particular symptoms being treated, the severity of the symptoms, responsiveness of the subject to the dried *Lactobacillus* formulation, the particular strain of microorganism in the dried formulation, and percent recovery of the microorganisms upon rehydration in vivo.

The dried bacterial formulation of the present invention can be delivered to a vaginal cavity using any means known in the art suitable for such delivery. In some embodiments, the dried formulation is delivered in the form of a suppository. Non-limiting exemplary suppositories suitable for use with the present invention can include gelatin capsules, and tablets. In some embodiments, the dried formulation is administered as a powder using an applicator. In some embodiments, the dried formulation can be rehydrated immediately prior to use and administered as a foam, cream, or paste. Additional modes of administration will be apparent to a person of ordinary skill in the art.

In some embodiments, a therapeutically effective amount of vaginal medicant of the present invention ranges from about $10^6$ to about $10^{12}$ CFUs per administration. In some embodiments, a therapeutically effective dose ranges from about between about $10^7$ to about $10^{11}$ CFUs per administration. In some embodiments, a therapeutically effective dose ranges from about $10^8$ to about $10^{10}$ CFUs per administration.

In some embodiments, the number of administrations ranges from about 1 to about 6 administrations per day. In some embodiments about 2 to about 3 administrations per day are required to achieve the desired effect. In some embodiments, the overall amount of viable bacteria (i.e. CFUs) administered per day is from about $10^6$ to about $10^{12}$ CFUs per day. In some embodiments, between about $10^7$ and about $10^{11}$ CFUs are administered per day. In some embodiments, about $10^8$ to about $10^{10}$ CFUs are administered per day. Persons of ordinary skill in the art will be readily able to determine optimal dosage, route of administration, and frequency of administration without undue experimentation.

VI. Examples

Example 1

**Fermentation and Manufacture of *Lactobacillus* Powders without Buffering**

This example details the general strategy for bacterial cultivation, suspension in preservation matrix, and drying. Note that this example does not include the addition of at least one buffering agent to the bacterial preparation. The basic procedure described here, for the culture and processing of *L. jensenii* 1153, is applicable for any microorganism suitable for use with the present invention.

A modified "draw and feed" fermentation strategy was employed to culture *L. jensenii* 1153. Specifically, the fermentation was carried out using an initial fed-batch fermentation followed by removal of a portion of the contents of the bioreactor and replacement of that material with fresh sterile MRS broth. The pH of the fermentation broth was maintained at pH 6.0 by the addition of ammonium hydroxide and potassium hydroxide. Each new fermentation began with an inoculum equivalent to the volume fraction that remained following the previous draw. For example, a 90% draw equated to a 10% inoculum for the next fermentation cycle. This draw and feed sequence was performed up to six times with 90% draws at the end of each cycle for a total production volume of 6.4 times the working volume (6 draws at 0.9 volumes plus the final draw at full volume) in media containing greater than $1\times10^9$ CFU/ml *L. jensenii* 1153.

Once the bacterial cell biomass was harvested, it was washed and resuspended in a preservation matrix as described in U.S. Pat. No. 6,372,209. The resultant mixture (cells resuspended in preservation matrix) was then spray dried onto a maltose dextrin seed in a 300N fluid bed drier (Applied Chemical Technology, Inc.). In a typical preparation as described above, maltose dextrin accounted for approximately 70% of the dried powder, which was then filled into #3 gelatin capsules (140 mg powder per capsule on average). The capsules were then placed individually into a foil pouch containing a desiccant packet and sealed under nitrogen. Alternatively, the dried powder was sealed in a foil pouch containing a desiccant packet, following flush with nitrogen gas, and then stored either at room temperature or at 4° C.

Example 2

Cell Viability Assay

This example details a method for determining the viability of a particular dried bacterial preparation following rehydration. The present inventors observed that conventional methods for determining bacterial viability using membrane integrity dyes (e.g., LIVE/DEAD BacLight Bacterial Viability and counting kit (Molecular Probes, Eugene, Oreg.) typically overestimated the number of viable cells when compared to the actual number of colony forming units achieved upon plating the rehydrated bacteria on bacterial media plates. Specifically, numerous cells showing intact membrane integrity with the commercially available kit were not able to form colonies when cultured on bacterial media plates.

Because of the overestimation of cell viability with the commercially available kits, the following procedure was used to determine cell viability as colony forming units (CFU/ml). Total cell counts were done using an Olympus IX51 microscope with a dark field condenser and a Petroff-Hausser counting chamber (0.01 mm in depth). Live cell count was determined based on CFU/ml on MRS plates. Prior to the actual count, 100 mg of dried powder formulation was rehydrated in 10 ml MRS broth (pH 6.2) at 37° C. for 30 minutes. Total cell counts were then done and various dilutions then plated on the MRS plates, which were then incubated for typically 48 hours prior to counting. Viability was then expressed as a ratio of CFU per ml/total cells per ml.

Example 3

Effects of Acidic Culture Conditions and Growth Phase at Harvest on Tolerance to Desiccation

This example tests the hypothesis that *Lactobacillus* cultured under acidic conditions or harvested at a stationary growth phase are more tolerant to desiccation than cells cultured under neutral pH or harvested during log phase. See, e.g., Corcoran et al. (2005) *Environ. Microbiol.* 71:3060-3067. To test this hypothesis, *L. crispatus* CTV-05 was fermented to late log phase at a constant pH of 5.0 or 6.0, or to a stationary phase at a pH of 6.0.

Microscopic examination of the bacteria following Gram staining revealed that the cells grown at a pH of 5.0 showed a "more stressed" phenotype exhibited by shorter and slightly thinner chains of rod-shaped cells compared to the cells grown at a pH of 6.0.

Cells were then harvested, resuspended in preservation matrix and dried in a fluid bed drier as described in Example 1. Following rehydration, the cell viability was determined as described above in Example 2. The recovery of viable bacteria rehydrated in MRS broth was similar for all three conditions (see, Table 1 below). Notably, when the dried *Lactobacillus* preparations were rehydrated in simulated vaginal fluid (pH 4.2) and then plated on MRS agar plates, the recovery of the cells grown at pH 5.0 and harvested at log phase was considerably lower (by approximately 30-fold) compared to the other two conditions grown at pH 6.0.

In contrast to the previous reports by Cochran et al. (2005) the present results indicate pH of the culture conditions has a greater impact on recovery than the growth phase at the time of harvest. In particular, as shown in Table 1, cells grown at pH 5.0 were considerably more sensitive to acid stress upon rehydration than cells grown at a pH of 6.0, regardless of the growth phase at the time of harvest.

TABLE 1

Effect of fermentation pH on cell recovery

| Fermentation pH | Recovery of *L. crispatus* CTV-05 in MRS broth pH 6.2 | Recovery of *L. crispatus* CTV-05 in simulated vaginal fluid pH 4.2 |
| --- | --- | --- |
| Log phase pH 6.0 | $2.7 \times 10^8$/140 mg dried powder | $1.6 \times 10^7$/140 mg dried powder |
| Stationary phase pH 6.0 | $2.1 \times 10^8$/140 mg dried powder | $1.2 \times 10^7$/140 mg dried powder |
| Log phase pH 5.0 | $2.5 \times 10^8$/140 mg dried powder | $6.0 \times 10^5$/140 mg dried powder |

Cell recovery of dried *L. crispatus* CTV-05. Dried powder (140 mg) was dissolved into 10 ml of MRS broth or simulated vaginal fluid, respectively. Cell suspensions were then incubated at 37° C. for 30 minutes and then plated onto MRS agar plates. CFUs were counted following 48 hour incubation.

Figure 2:
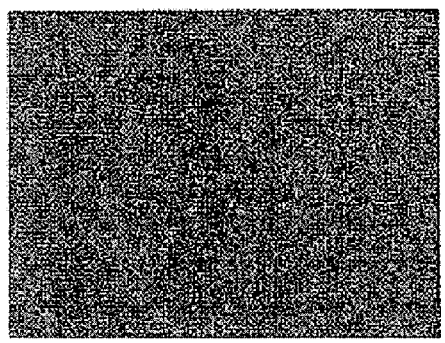
FIG. 2 shows cell recovery of manufactured *L. jensenii* 1153 on MRS agar, following rehydration in simulated vaginal fluid (pH 4.2) prepared according to Moosa et al. (2004) *Antimicrob. Agents Chemother.* 48:161-167, or MRS broth (pH 6.2). One hundred forty mg of *L. jensenii* 1153 powder was dissolved into 10 ml of simulated vaginal fluid or MRS broth. Cell suspensions were incubated at 37° C. for 30 minutes and then plated on MRS plates for CFU determination.
Figure 2:
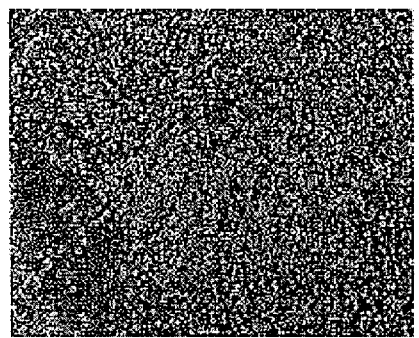

To confirm that these effects were not strain specific, we examined the viability of a dried preparation of *L. jensenii* 1153 in preservation matrix, manufactured according to Example 1. One hundred forty mg of dried *L. jensenii* 1153 formulation was incubated with solutions having different osmolarity for 30 minutes at 37° C. before plating onto MRS agar plates to determine viability. The results showed that *L. jensenii* 1153 grew well after rehydration in MRS broth (pH 6.2) but exhibited poor recovery in simulated vaginal fluid (SVF) pH 4.2. See, FIG. 2.

Not surprisingly, the non-buffered dried preparation of *L. jensenii* 1153 showed significantly reduced vaginal colonization in vivo using a Chinese rhesus macaques (*Macaca mulatta*) animal model that we have previously established as a non-human primate model for vaginal colonization. These results led us to modify the manufacturing formulation as detailed in Example 4 below.

Example 4

Effect of pH on Cell Recovery of Dried *L. Jensenii* 1153 Rehydrated in Simulated Vaginal Fluid (pH 4.2)

Figure 3:
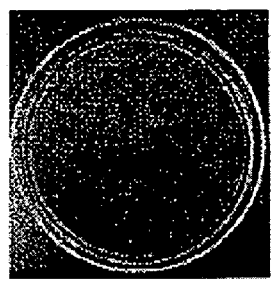
FIG. 3 shows the effect of pH on cell recovery of manufactured *L. jensenii* 1153 rehydrated in simulated vaginal fluid (SVF). Cells were recovered on MRS agar, following incubation of manufactured *L. jensenii* 1153 with or without buffers in simulated vaginal fluid, pH 4.2.
Figure 3:
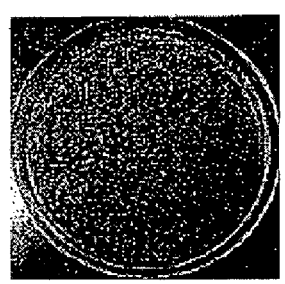
Figure 3:
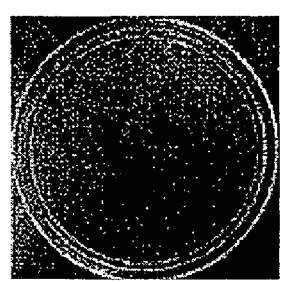
Figure 3:
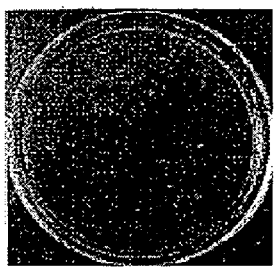
Figure 3:
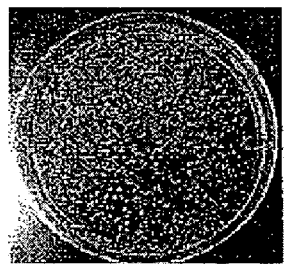
Figure 3:
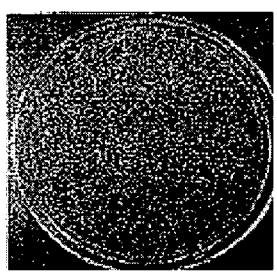

This example shows that a slight increase in pH by addition of at least one buffering agent, such as arginine, $NaHCO_3$, or $Na_2HPO_4$ to the non-buffered dried *L. jensenii* 1153 preparation significantly improved cell recovery in simulated vaginal fluid (SVF). See, FIG. 3.

Dried *L. jensenii* 1153 preparations were tested with various buffering agents shown in Table 2. Specifically, 140 mg of the buffered dried formulation was dissolved in simulated vaginal fluid (pH 4.2). The pH of the resultant solution was measured and cell viability was then determined by measuring CFUs as described in Example 2. The results showed that cell recovery reached a plateau at a pH ranging from about 7.0 to about 8.2 with dried *Lactobacillus* powders supplemented with $Na_2HPO_4$ (with or without NaCl), $NaHCO_3$, and/or Arginine (see Table 2). Optimal buffering of dried *L. jensenii* 1153 powders resulted in an improved cell recovery in simulated vaginal fluid by log 6 CFU.

TABLE 2

Cell recovery at different pH in a simulated biological fluid

|  | pH | CFU/140 mg powder |
|---|---|---|
| Na2HPO4 (mM) in SVF | | |
| 0 | 4.29 | $4.0 \pm 0.6 \times 10^3$ |
| 6.25 | 4.82 | $1.3 \pm 0.2 \times 10^4$ |
| 12.5 | 4.95 | $1.1 \pm 0.2 \times 10^5$ |
| 25 | 6.58 | $5.1 \pm 0.9 \times 10^8$ |
| 50 | 6.93 | $8.1 \pm 0.5 \times 10^8$ |
| 100 | 7.39 | $1.1 \pm 0.6 \times 10^9$ |
| 200 | 7.78 | $8.7 \pm 1.8 \times 10^8$ |
| 400 | 8.13 | $3.9 \pm 0.3 \times 10^8$ |
| 800 | 8.5 | $2.0 \pm 1.0 \times 10^8$ |
| Phosphate salts (mM) in SVF | | |
| 6.25 | 4.49 | $3.0 \pm 0.6 \times 10^4$ |
| 12.5 | 4.86 | $3.8 \pm 1.1 \times 10^5$ |
| 25.0 | 5.88 | $2.3 \pm 0.8 \times 10^7$ |
| 50 | 6.54 | $3.8 \pm 0.2 \times 10^8$ |
| 100 | 6.86 | $6.1 \pm 0.8 \times 10^8$ |
| 200 | 7.04 | $6.0 \pm 0.1 \times 10^8$ |

TABLE 2-continued

Cell recovery at different pH in a simulated biological fluid

|  | pH | CFU/140 mg powder |
|---|---|---|
| 400 | 7.2 | $1.9 \pm 0.2 \times 10^8$ |
| 800 | 7.26 | $6.0 \pm 1.3 \times 10^7$ |
| NaHCO3 (mM) in SVF | | |
| 6.25 | 4.68 | $1.1 \pm 0.4 \times 10^4$ |
| 12.5 | 5.21 | $3.6 \pm 1.7 \times 10^5$ |
| 25 | 6.95 | $1.4 \pm 0.1 \times 10^8$ |
| 50 | 7.93 | $1.2 \pm 0.04 \times 10^8$ |
| 100 | 8.22 | $2.0 \pm 0.2 \times 10^7$ |
| 200 | 8.55 | $5.4 \pm 1.1 \times 10^6$ |
| 400 | 8.74 | $4.2 \pm 0.6 \times 10^6$ |
| 800 | 8.76 | $4.6 \pm 0.3 \times 10^6$ |
| Arginine (mM) in SVF | | |
| 6.25 | 4.74 | $8.5 \pm 0.6 \times 10^3$ |
| 12.5 | 5.28 | $2.4 \pm 1.1 \times 10^5$ |
| 15 | 5.66 | $1.3 \pm 0.2 \times 10^6$ |
| 17.5 | 6.55 | $2.5 \pm 0.8 \times 10^7$ |
| 20 | 8.10 | $1.2 \pm 0.1 \times 10^8$ |
| 25 | 8.92 | $8.4 \pm 0.1 \times 10^7$ |
| 50 | 9.65 | $2.3 \pm 0.3 \times 10^5$ |
| 100 | 10.32 | $3.8 \pm 0.7 \times 10^3$ |
| 200 | 10.7 | $7.2 \pm 0.2 \times 10^2$ |

Figure 4:
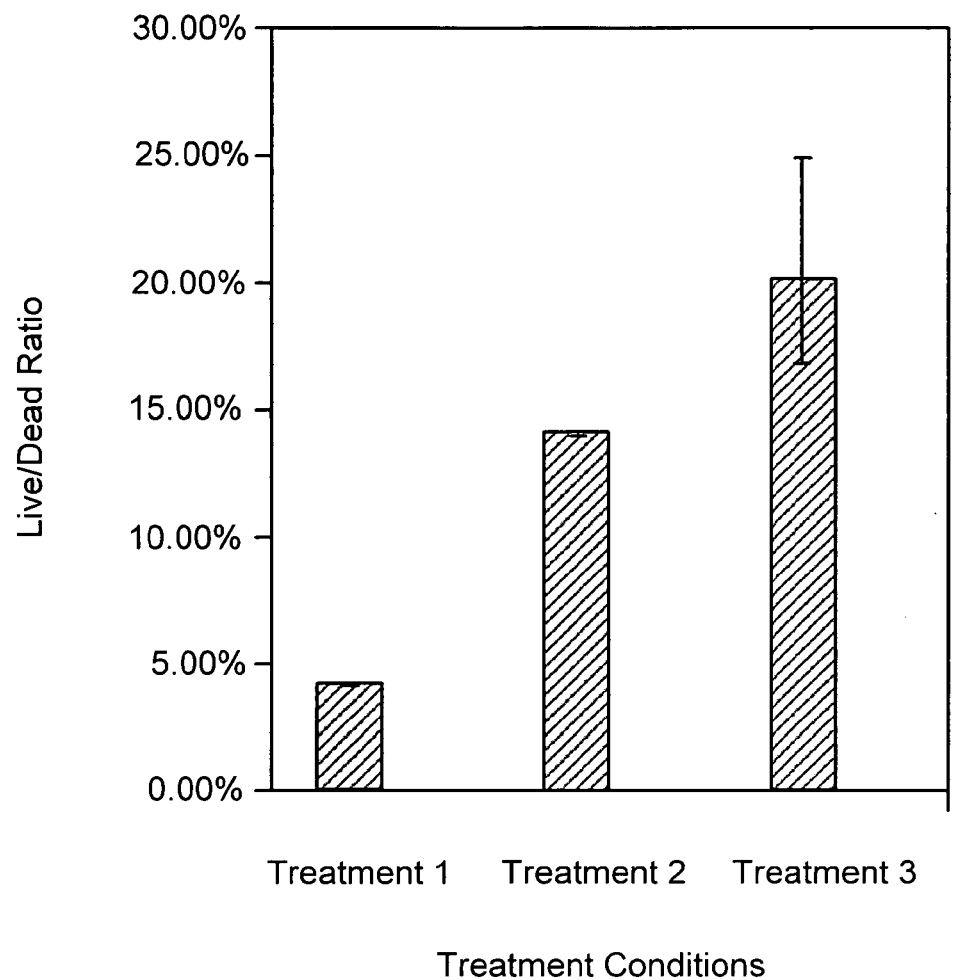
FIG. 4 shows Live/dead cell ratio for various dried *L. jensenii* 1153 preparations. These preparations included cells not washed with a buffer (Treatment 1), cells washed with a buffer, but without buffering in preservation in matrix (Treatment 2), and cells washed with a buffer and suspended in a buffered preservation matrix (Treatment 3).

Based on the above results, we added a wash step to the cells following bacterial fermentation to achieve a more neutral pH. We also added a buffer to the cell paste to achieve a neutral pH in the preservation matrix prior to fluid bed drying. This modified manufacturing process lead to a dramatic (4-5-fold) improvement in the live/dead ratio of dried β-glucuronidase (GusA)-expressing *L. jensenii* 1153, as can be seen in FIG. 4. A good cell viability was achieved for strains of *L. gasseri*, when dried and preserved in buffered preservation matrix (data not shown).

Example 5

Functional Test for Buffered Formulation

This example demonstrates a simple functional test to measure the buffering capacity of a dried bacterial formulation. In this example, two different *Lactobacillus* species were tested with various buffer formulations. Specifically, the parental strain of *L. jensenii* 1153 (denoted as A in table 3) and the bioengineered *L. jensenii* 1153 strain having the GusA expression cassette stably integrated into the *Lactobacillus* chromosome (denoted as B in table 3) were tested. Each strain was prepared as a dried preparation (example 3) modified to include a buffering composition as shown in Table 3.

The buffering capacity of the dried formulations was determined by dissolving 140 mg of the dried *Lactobacillus* powdered formulation in 3 ml of water. The resultant pH of the solution was then measured as shown in Table 3. The solutions were then titrated to a pH below 4.2 using either 0.1N HCl or 1N lactic acid. The minimum volume of acid required to titrate the solution to a pH below 4.2 and the effective pH range for the buffer is shown in Table 3.

TABLE 3

Functional test of buffering agents

| Buffered *Lactobacillus* | Starting pH (in 3 ml H$_2$O) | Volume of 0.1N HCl | Volume of 1N lactic acid | Buffer pk$_a$ at 20° C. | Effective pH range |
|---|---|---|---|---|---|
| A + 100 mM Na$_2$HPO$_4$ | 8.7 | 250 μl | 380 μl | 2.1, 7.2, 12.3 | 5.8-8.0 |
| B + 100 mM Na$_2$HPO$_4$ | 8.6 | 250 μl | 410 μl |  |  |

TABLE 3-continued

Functional test of buffering agents

| Buffered Lactobacillus | Starting pH (in 3 ml H$_2$O) | Volume of 0.1N HCl | Volume of 1N lactic acid | Buffer pk$_a$ at 20° C. | Effective pH range |
|---|---|---|---|---|---|
| A + 100 mM PBS | 7.3 | 250 μl | 330 μl | 2.1, 7.2, 12.3 | 5.8-8.0 |
| B + 100 mM PBS | 7.2 | 200 μl | 300 μl | | |
| A + 25 mM NaHCO$_3$ | 8.2 | 70 μl | 115 μl | 6.3 | 5.0-8.0 |
| B + 25 mM NaHCO$_3$ | 8.0 | 70 μl | 110 μl | | |
| A + 20 mM L-Arginine | 10.0 | 60 μl | 90 μl | 2.0, 9.0, 12.5 | Broad range |
| B + 20 mM L-Arginine | 10.0 | 60 μl | 90 μl | | |

The results demonstrate that the effective pH range for the buffers is typically between pH 5.0 and pH 8.0. Furthermore, using this simple functional test, a skilled artisan can readily determine if a particular dried bacterial formulation falls within the scope of the instant invention.

It is understood that the examples and embodiments described herein are for illustrative purposes only, and that various modifications or changes in light thereof will be suggested to persons of skill in the art and are to be included within the spirit and purview of this application and the scope of the appended claims. All publications, patents, and patent applications cited herein are hereby incorporated by reference in their entirety for all purposes.

What is claimed is:

1. A method of colonizing vaginal mucosa with a *Lactobacillus* species, comprising contacting a vaginal wall with a dried formulation of live *Lactobacillus* where the formulation contains at least one buffer having a pk$_a$ of at least 4.3, and
wherein 140 mg of the formulation in 3 ml of water is capable of maintaining a pH above 6.0 with the addition of 60 μl of 0.1N HCl.

2. The method of claim 1, wherein the *Lactobacillus* species is selected from the group consisting of *L. crispatus, L. jensenii, L. gasseri, L. johnsonii, L. fermentum, L. vaginalis, L. acidophilus, L. gallinarum, L. coleohominis,* and *L. iners*.

3. The method of claim 1, wherein the *Lactobacillus* species is *L. crispatus*.

4. The method of claim 1, wherein the *Lactobacillus* species is *L. jensenii*.

5. The method of claim 1, wherein the *Lactobacillus* species is *L. gasseri*.

6. The method of claim 1, wherein a buffer is selected from the group consisting of Na$_2$HPO$_4$, phosphate salts, NaHCO$_3$, and arginine.

7. The method of claim 1, wherein a buffer is present in a concentration range from about 25 mM to about 200 mM.

8. The method of claim 1, wherein 140 mg of the formulation in 3 ml of water maintains a pH above 7.0 with the addition of 60 μl of 0.1N HCl.

9. The method of claim 1, wherein 140 mg of the formulation in 3 ml of water maintains a pH above 8.0 with the addition of 60 μl of 0.1N HCl.

10. The method of claim 1, wherein 140 mg of the formulation in 3 ml of water maintains a pH of between 6 and 8.2 with the addition of 60 μl of 0.1N HCl.

* * * * *